United States Patent [19]

Suzuki et al.

[11] Patent Number: 5,127,079
[45] Date of Patent: Jun. 30, 1992

[54] MULTIFILAMENT TYPE PLASTIC OPTICAL FIBER ENDOSCOPE

[75] Inventors: Fumio Suzuki; Masashi Okamoto; Toshinori Sumi, all of Otake; Naoyuki Fukahori, Tokyo, all of Japan

[73] Assignee: Mitsubishi Rayon Company Ltd., Tokyo, Japan

[21] Appl. No.: 658,869

[22] Filed: Feb. 22, 1991

[30] Foreign Application Priority Data

Feb. 23, 1990 [JP] Japan .................................. 2-41189

[51] Int. Cl.$^5$ .................................................. G02B 23/26
[52] U.S. Cl. ................................................ 385/117; 385/116
[58] Field of Search ............... 350/96.24, 96.25, 96.26; 385/115, 116, 117

[56] References Cited

U.S. PATENT DOCUMENTS

| | | | |
|---|---|---|---|
| 4,690,500 | 9/1987 | Hayami et al. | 350/96.25 |
| 4,768,857 | 9/1988 | Sakunaga et al. | 350/96.24 |
| 4,772,093 | 9/1988 | Abele et al. | 350/96.25 |
| 4,812,012 | 3/1989 | Terada et al. | 350/96.24 |
| 4,842,365 | 6/1989 | Terada et al. | 350/96.24 |
| 4,872,740 | 10/1989 | Terada et al. | 350/96.26 |
| 4,964,692 | 10/1990 | Prescott | 350/96.24 |

FOREIGN PATENT DOCUMENTS 250209 12/1987 European Pat. Off. .
279576 8/1988 European Pat. Off. .

Primary Examiner—John D. Lee
Attorney, Agent, or Firm—Oblon, Spivak, McClelland, Maier & Neustadt

[57] ABSTRACT

An endoscope comprising as an image-transmitting member a multifilament type plastic optical fiber in which 50 to 20,000 islands having a core-sheath structure, a core diameter of 2 to 70 μm and a circular or substantially circular section are arranged in a zigzag-stacked or square-stacked structure in the sea having a circular or substantially circular section, so that the lamination structure of the entire cores has a substantially circular shape in the section of the image-transmitting portion, wherein the same positional relationship of the ends of light-transmitting paths arranged in the section of the optical fiber is maintained on both the ends of the optical fiber, the periphery of the section of the image-transmitting portion of the optical fiber has a circular or substantially circular shape, and an object lens is attached to one end of the image-transmitting member and an image-transmitting light-receiving member is arranged on the other end of the image-transmitting member.

10 Claims, 3 Drawing Sheets

MULTIFILAMENT TYPE PLASTIC OPTICAL FIBER ENDOSCOPE

BACKGROUND OF THE INVENTION

1. Field of the Invention

The present invention relates to an endoscope comprising, as an image-transmitting member, a multifilament type plastic optical fiber cable in which the section of an image-transmitting portion has a circular or substantially circular shape, which endoscope has a good elasticity can observe even the interior of a narrow blood vessel, and can be effectively utilized as a medical endoscope.

2. Description of the Related Art

With the recent increase of the number of patients suffering from heart diseases, the development of a blood vessel endoscope capable of observing the interior of the coronary arteries is urgently required, and an endoscope comprising, as an image-transmitting member, an optical fiber bundle composed of a great number of bundled glass type optical filaments having a diameter of 10 to 50 $\mu$ has been developed. Nevertheless, since the glass type optical fiber bundle is rigid and easily broken, it is difficult to pass an endoscope comprising an image-transmitting member composed of glass type optical filaments bundle through the curved and bent coronary arteries, and even if the endoscope can be passed through the coronary arteries, if the filaments are broken this will be life-endangering, and thus the endoscope cannot be practically used. Although a throwaway type blood vessel endoscope is desirable, for example, to avoid infection with AIDS and the like, this desire cannot be satisfied by the glass type optical fiber due to the high cost thereof.

An endoscope comprising an image-transmitting member composed of a multifilament type plastic optical fiber cable also is being developed, and among multifilament type plastic optical fiber cable regarded as being capable of transmitting images, those having a circular section in the image-transmitting portion are disclosed in Japanese Unexamined Patent Publication No. 56-39505 and Japanese Examined Patent Publication No. 59-14570. Nevertheless, in these multifilament type plastic optical fiber cable, as shown in Japanese Examined Patent Publication No. 59-14570, the sections of islands acting as light-transmitting paths in the section of the image-transmitting portion are deformed from the circular shape and have a polygonal shape, and therefore, the light-transmitting characteristics of the light-transmitting paths at the center of the section of the image-transmitting portion of the multifilament type optical fiber cable are substantially different from those of the light-transmitting paths in the peripheral portion of the section of the image-transmitting portion. Accordingly, it is impossible to transmit a sharp image, and such a multifilament type optical fiber cable cannot be utilized as the image-transmitting member of a blood vessel endoscope.

Blood vessel endoscopes having improved performances have been proposed in U.S. Pat. No. 4,872,740, Japanese Unexamined Patent Publication No. 63-197190 and Japanese Unexamined Patent Publication No. 64-908, and in the plastic image-transmitting member used for these endoscopes, light transmitting paths having a substantially circular sectional shape are arranged in a hexagonal staggered form structure in the section of a multifilament type optical fiber cable having an image-transmitting portion having a substantially rectangular peripheral shape, and therefore, the respective light transmitting paths have a substantially circular shape to hexagonal sectional shape. A multifilament plastic optical fiber cable of this type has superior image-transmitting characteristics to those of the conventional multifilament type plastic optical fibers, and it is thought that the plastic optical fiber cable of this type can be used for an endoscope.

Nevertheless, as the result of the investigation made by the present inventors, it was found that multifilament type plastic optical fiber cable as mentioned above have a anisotropy of the flexural regidity and the flexural rigidity in a direction diagonal in the rectangular section of the image-transmission portion that is too large for use as an image-transmitting member of an endoscope, and therefore, it is very difficult to put these plastic optical fibers to practical use.

SUMMARY OF THE INVENTION

The present inventors carried out research with a view to obtaining a multifilament type plastic optical fiber cable having an image-transmitting portion having a circular section and capable of being used as an image-transmitting member of a vessel blood endoscope, and as a result, found that the problems of the conventional techniques are fully resolved by using an image-transmitting member having a novel structure in which light-transmitting paths having a substantially circular section are disposed in a square-stacked or hexagonal staggered form arrangement in an image-transmitting portion having a substantially circular section. The present invention is based on this finding.

More specifically, in accordance with the present invention, there is provided an endoscope comprising, as an image-transmitting member, a multifilament type plastic optical fiber cable in which 50 to 20,000 light transmitting path having the path diameter of 2 to 70 $\mu$m and a circular or substantially circular section are arranged in a hexagonal staggered form or square-stacked structure in a circular or substantially circular cable section, so that the configuration structure of the entire core has a substantially circular shape in the section of the image-transmitting portion, wherein the same positional relationship of the ends of light-transmitting paths arranged in the section of the multifilament type optical fiber cable is maintained at both ends of the multifilament type optical fiber cable, the periphery of the section of the image-transmitting portion of the optical fiber cable has a circular or substantially circular shape, and an object lens is attached to one end of the image-transmitting member and an image-transmitting light-receiving member is arranged on the other end of the image-transmitting member.

DESCRIPTION OF THE PREFERRED EMBODIMENTS

Figure 1:
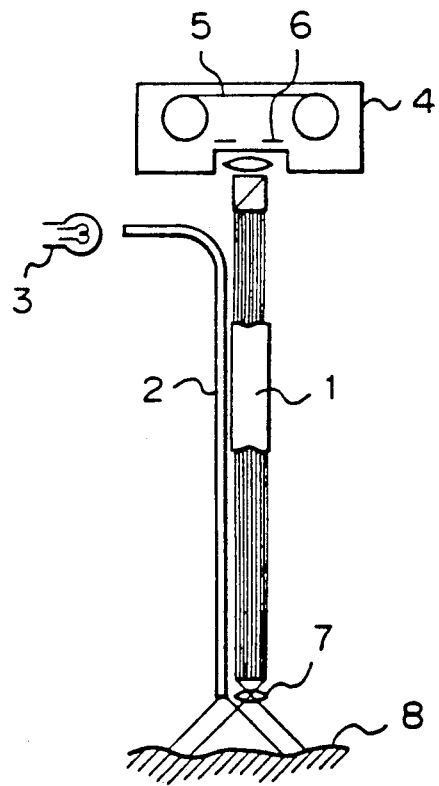
FIG. 1, 5 and 6 are sectional diagrams illustrating of the endoscope of the present invention.

In the multifilament type plastic optical fiber cable constituting the image-transmitting member in the present invention, the diameter of the section of cores of the light-transmitting paths is 2 to 70 μm, preferably 2 to 20 μm, more preferably 3 to 10 μm. If the diameter of the section of cores is smaller than 2 μm, the light-transmitting property is greatly reduced and the image-transmitting property becomes poor. On the other hand, if the diameter of the section of cores exceeds 70 μm, the resolving power of the multifilament type optical fiber is reduced and the rigidity increased, and the characteristics of the optical fiber cable as the image-transmitting member of an endoscope become poor. The section of cores should have a circular or substantially circular shape. Namely, to obtain uniform light-transmitting characteristics in the multifilament type plastic optical fiber cable, the section of cores should have a circular shape or a hexagonal or higher polygonal shape. The number of the light-transmitting paths arranged in the section of the multifilament type optical fiber cable is 50 to 20,000, preferably 500 to 20,000, more preferably 1,500 to 20,000. If the number of light-transmitting path is smaller than 50, the image-observing property of the image-transmitting member becomes poor, and if the number of the light transmitting path is larger than 20,000, the rigidity of the multifilament type optical fiber cable becomes too high and the characteristics as the image-transmitting member become poor.

The most characteristic feature of the novel multifilament type optical fiber cable used as the image-transmitting member in the present invention resides in that the light-transmitting paths are disposed in a square-stacked or hexagonal staggered form arrangement in the circular section of the image-transmitting portion and the section of the arrangement structure of the entire cores has a substantially circular shape. If the arrangement of the light transmitting paths in the section of the image-transmitting member is different from the square-stacked or hexagonal staggered form arrangement, as shown in Japanese Examined Patent Publication No. 59-14570, although the sectional shape of the light-transmitting paths arranged in the central portion of the image-transmitting member is substantially circular, the sectional shape of the light-transmitting paths arranged in the peripheral portion of the section of the image-transmitting member have different shapes, such as oblong, square and pentagonal, and the light-transmitting characteristics of the respective light transmitting paths are different from one another, and the multifilament type optical fiber cannot be used as the image-transmitting member.

In contrast, in the multifilament type optical fiber cable used in the present invention, light-transmitting paths having a circular section are disposed in a square-stacked or hexagonal staggered form in the circular section of the image-transmitting portion, and therefore, the sectional shape of the paths arranged in the central portion of the section of the image-transmitting portion and the path arranged in the peripheral portion of the section of the image-transmitting portion are substantially equal to one another, and the difference of the light-transmitting characteristics among these paths is not large and a very sharp image can be transmitted.

Figure 2:
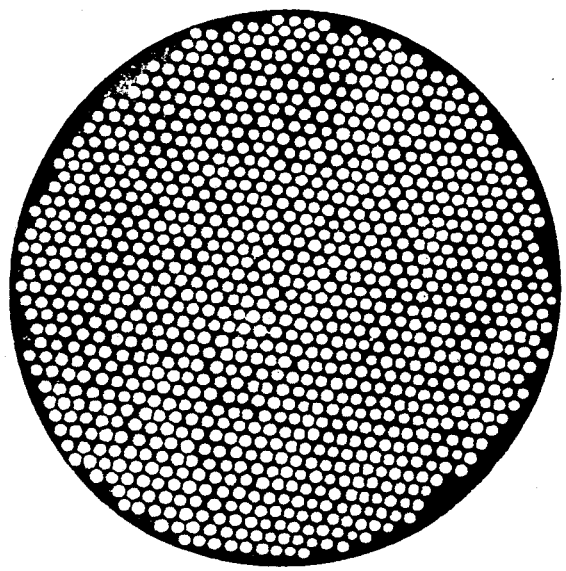
FIG. 2 is an enlarged microscope view showing the section of a multifilament type plastic optical fiber cable constituting the image-transmitting member of the endoscope of the present invention.

Moreover, in the multifilament type plastic optical fiber of the present invention, as shown in FIG. 2, the paths are substantially circularly arranged in the section of the image-transmitting portion, and therefore, there is no substantial anisotropy of the flexural rigidity in the optical fiber and the fiber has a pliability such that the fiber can be bent in any direction without a feeling of any substantial resistance. Accordingly, the optical fiber cable of the present invention has excellent characteristics as the image-transmitting member for a blood vessel endoscope.

Referring to FIG. 1, which is a schematic diagram illustrating one embodiment of the endoscope of the present invention, this endoscope comprises a light source system for guiding illuminating light to an object 8 to be observed, from a light source 3, for example, a light-transmitting optical fiber 2, an optical system for focusing an image of the object 8 on the top end of the multifilament optical fiber, for example, an object lens 7, and a multifilament type plastic optical fiber 1 for guiding the focused image precisely to an image-receiving portion, for example, a still camera 4. Note, in the still camera 4, reference numeral 5 represents a film and reference numeral 6 represents a shutter.

Figure 3:
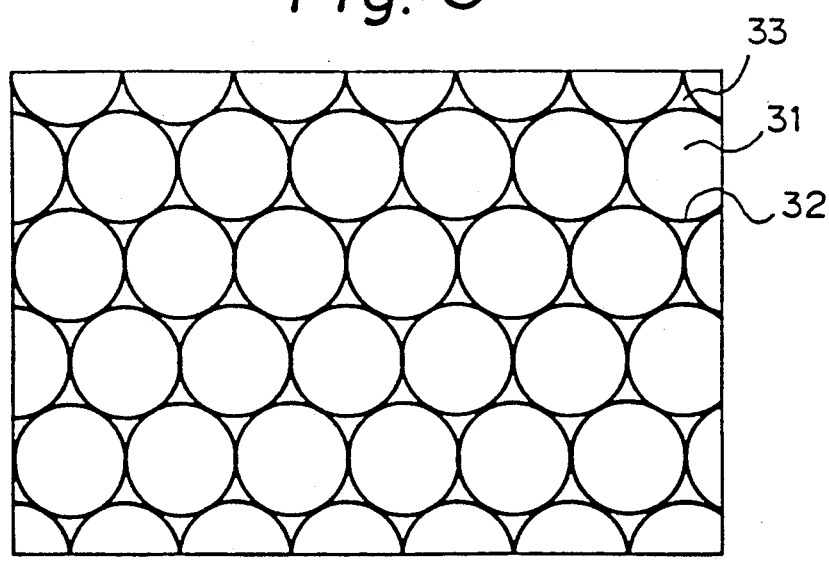
FIG. 3 is an enlarged electron microscope view showing a part of the section shown in FIG. 2; and, FIG. 4 is a sectional diagram illustrating a spinneret preferably used for preparing a multifilament type plastic optical fiber cable used as the image-transmitting member in the present invention.

The most characteristic feature of the endoscope of the present invention resides in that a multifilament type plastic optical fiber cable having an excellent flexibility is used as the image-transmitting member. A multifilament type plastic optical fiber cable having 3043 light-transmitting paths arranged in a hexagonal staggered form structure is shown as an example in the enlarged microscope sectional view of FIG. 2, and a part of this multifilament type optical fiber cable is shown in the enlarged electron microscope sectional view of FIG. 3. In FIG. 3, reference numerals 31 and 32 represent a light transmitting path having core-sheath structure, reference numeral 31 represents a core of the light-transmitting path and reference numeral 32 represents a sheath of the path, and reference numeral 33 represents the sea portion surrounding the light-transmitting path.

To maintain a good image-transmitting property, preferably the light transmission loss is not increased. From this viewpoint, the section of each light transmitting path preferably has a substantially uniform hexagonal or more polygonal shape resembling a circular shape. In the present invention, preferably the light transmission loss of the multifilament type optical fiber cable is smaller than 6 dB/m, more preferably smaller than 3 dB/m, especially smaller than 1.5 dB/m.

Since the peripheral shape of the lens to be used as the object lens is generally circular, and the sectional shape of the endoscope is also circular, in view of the handling property at the assembling step, the image-transmitting portion of the multifilament type optical fiber cable used as the image-transmitting member preferably has a circular section. Especially, in the case of a blood vessel endoscope in which at the diameter of the section must be reduced and there must be no anisotropy of the flexural rigidity, preferably a multifilament type optical fiber cable having an image-transmitting portion having a circular section, which makes it possible to effectively utilize the section of the endoscope, is used as the image-transmitting member. Also, the light-transmitting member must have an excellent flexibility so that the wall face of a blood vessel is not damaged when the image-transmitting member is inserted into the blood vessel, and in particular, the image-transmitting member must have a property such that the flexibility does not differ according to the bending direction. An image-transmitting member having a rectangular section cannot be used for this purpose, and a multifilament type optical fiber cable having an image-transmitting portion having a circular or substantially circular section is preferably used because the optical fiber cable has uniform flexural characteristics.

The number of the light transmitting paths arranged in the section of the image-transmitting portion is in the range of from 50 to 20,000, and the core occupancy ratio of the total section of the image-transmitting portion is at least 30%, preferably 50 to 95%. When a multifilament type plastic optical fiber cable in which the core occupancy ratio and the number of the light transmitting paths satisfy the above-mentioned requirements is used as the image-transmitting member, the quantity of transmitted light is greatly increased over the quantity of light transmitted by the conventional multifilament type optical fiber cable heretofore used for the endoscope, and a sharp and bright image can be obtained.

The brightness index I defined by the following formula (I) is preferably adopted for evaluating the quantity of transmitted light and the image-transmitting property of the multifilament type plastic optical fiber cable used in the present invention:

$$I = S \cdot NA^2 \cdot 10^{-\left(\frac{aL}{10}\right)} \quad (I)$$

wherein S is the occupancy ratio of cores in the multifilament type optical fiber cable, $a$ is the transmission loss (dB/m) per meter of the multifilament type optical fiber cable, NA is the numerical aperture, and L is the length (m) of the used multifilament type optical fiber. The brightness index I of the multifilament type plastic optical fiber cable of the present invention is preferably at least $2.0 \times 10^{-2}$, more preferably at least $4.5 \times 10^{-2}$, especially at least $5 \times 10^{-2}$.

To obtain a multifilament plastic optical fiber cable having this brightness index, the occupancy ratio of the total core section in the sectional area of the image-transmitting portion should be at least 30%, preferably at least 50%, more preferably at least 60%.

The numerical aperture NA is defined by the following formula (II):

$$NA = \sqrt{n_1^2 - n_2^2} \quad (II)$$

wherein $n_1$ is the refractive index of the core-forming plastic material and $n_2$ is the refractive index of the sheath-forming plastic material.

In the present invention, the difference between the refractive index $n_1$ of the core-forming polymer and the refractive index $n_2$ of the sheath-forming polymer in the light transmitting paths is at least 0.01, and the core-forming polymer having the refractive index $n_1$ and the sheath-forming polymer having the refractive index $n_2$ is selected so that the numerical aperture NA defined by the formula (II) is at least 0.16, especially at least 0.3. Where the NA value is at least 0.16, a multifilament type optical fiber having a brightness index of at least $2 \times 10^{-3}$ can be effectively prepared.

To maintain a good sharpness and brightness in the transferred image, preferably L is smaller than 10.

To obtain a transferred image having a good resolution, preferably the core diameter of the light-transmitting paths constituting the multifilament type optical fiber is 2 to 70 μ.

If the multifilament type plastic optical fiber acting as the image-transmitting member of the endoscope of the present invention has an image transfer characteristic such that, when a converging lens and a light-receiving face are disposed at both ends of the multifilament type optical fiber cable and a test pattern of a resolution test target (USFA 1951) is transmitted by white light according to the method of USFA 1951, the resolution is at least 2 line pairs/mm where each line pair consists of one white line and one black line, a sharp and bright image can be transferred.

Furthermore, the multifilament type plastic optical fiber cable used in the present invention is characterized in that the optical fiber cable can transfer a sharp image even in the state where the optical fiber is wound on a rod having a diameter of 10 mm by 3 to 20 turns. The endoscope of the present invention comprising this multifilament type optical fiber as the image-transmitting member is advantageous in that the image-transmitting member is not broken, the handling property is good, and any pain felt by a patient is greatly moderated.

Figure 4:
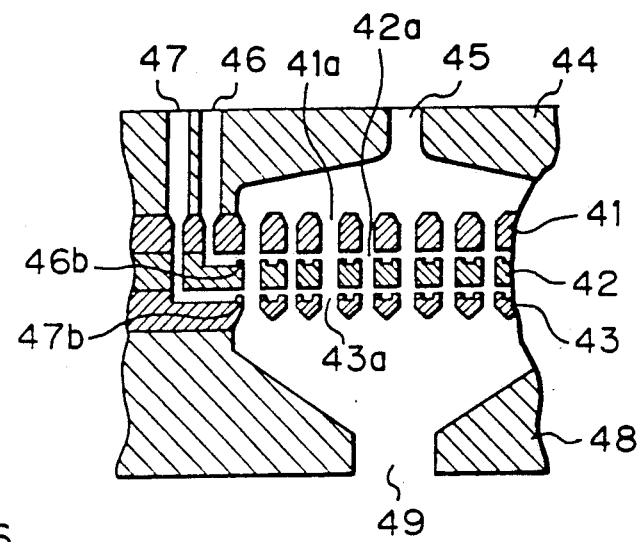
Figure 5:
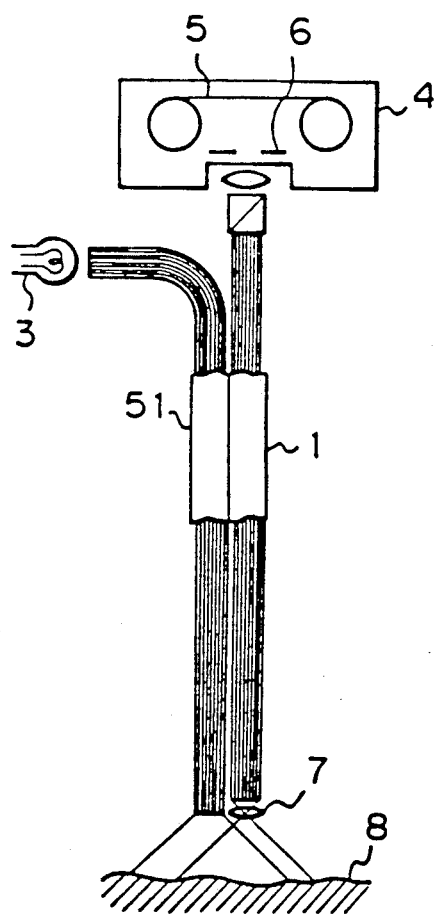

The multifilament type optical fiber cable used as the image-transmitting member in the present invention is preferably prepared according to the conjugate spinning process using a spinneret having a sectional structure as shown in FIG. 4, where a light-transmitting portion of a core-sheath structure comprising image-transmitting cores and sheaths surrounding the cores is integrated into an image-transmitting member having a circular section by using a sea component.

As examples of the plastics for forming the core, sheath and sea components of the multifilament type optical fiber used in the present invention, there can be mentioned polymethyl methacrylate (n=1.49), copolymers (n=1.47 to 1.50) composed mainly of methyl methacrylate, polystyrene (n=1.58), copolymers (n=1.50 to 1.58) composed mainly of styrene, styrene/acrylonitrile copolymers (n=1.56), poly-4-methylpentene-1 (n=1.46), ethylene/vinyl acetate copolymers (n=1.46 to 1.50), a polycarbonate (n=1.50 to 1.57), polychlorostyrene (n=1.61), polyvinylidene chloride (n=1.63), polyvinyl acetate (n=1.47), methyl methacrylate/styrene, vinyltoluene or α-methylstyrene/maleic anhydride terpolymers or quadripolymers (n=1.50 to 1.58), polydimethylsiloxane (n=1.40), polyacetal (n=1.48), polytetrafluoroethylene (n=1.35), polyvinylidene fluoride (n=1.42), polytrifluoroethylene (n=1.40), polyperfluoropropylene (n=1.34), fluoroethylene copolymers or terpolymers (n=1.35 to 1.40), polyvinylidene fluoride/polymethyl methacrylate blends (n=1.42 to 1.46), copolymers composed mainly of a fluoromethacrylate represented by the general formula $CH_2=C(CH_3)COORf$ in which Rf stands for $(CH_2)_n(CF_2)_nH$ (n=1.37 to 1.42), $(CH_2)_n(CF_2)_nF$ (n=1.37 to 1.40), $CH-(CF_3)_2$ (n=1.38), $C(CF_3)_3$ (n=1.36), $CH_2CF_2CHFCF_3$ (n=1.40) or $CH_2CF(CF_3)_2$ (n=1.37), copolymers of these fluoromethacrylates (n=1.36 to 1.40), copolymers of such a fluoromethacrylate with methyl methacrylate (n=1.37 to 1.43), polymers composed mainly of a fluoroacrylate represented by the general formula $CH_2=CH.COOR'f$ in which R'f stands for $(CH_2)_m(CF_2)_nF$ (n=1.37 to 1.40), $(CH_2)_m(CF_2)_nH$ (n=1.37 to 1.41), $CH_2CF_2CHFCF_3$ (n=1.41) or $CH(CH_3)_2$ (n=1.38), copolymers of these fluoroacrylates (n=1.36 to 1.41), copolymers of such a fluoroacrylate and a fluoromethacrylate as described above (n=1.36 to 1.41), copolymers of these fluoroacrylate and fluoromethacrylate and methyl methacrylate (n=1.37 to 1.43), homopolymers and copolymers (n=1.37 to 1.42) composed mainly of a 2-fluoroacrylate represented by the general formula $CH_2=CF.COOF''f$ in which $R''f$ stands for $CH_3$, $(CH_2)_m(CF_2)_nF$, $(CH_2)_m(CF_2)_nH$, $CH_2CF_2CHFCF_3$ or $C(CF_3)_2$ and fluorine-containing alkyl fumaric acid ester polymers (n=1.30 to 1.42).

The multifilament type plastic optical fiber cable used as the image-transmitting member of the endoscope of the present invention can be effectively prepared according to the following process.

A core-forming nozzle, a sheath-forming nozzle and a sea-forming nozzle, in which the periphery of the spinning nozzle hole arrangement has a circular or substantially circular shape and the holes are arranged in a hexagonal staggered form structure or a square-stacked structure, are assembled as indicated by 41, 42 and 43 in FIG. 4, and a polymer-supplying orifice 44 is connected to a fiber-gathering orifice 48. Reference numeral represents a core-spinning hole, reference numeral 42a represents a sheath-spinning hole, reference numeral 43a represents a sea-spinning hole, reference numeral 45 represents a core-supplying hole, reference numeral 46 represents a sheath-supplying hole, reference numeral 47 represents a sea-supplying hole, and reference numeral 49 represents a gathering hole. Reference numeral 46b represents a sea component-overflowing projection and reference numeral 47b represents a sea component-overflowing projection, and these overflowing projections are arranged to surround the respective nozzle holes.

The core component supplied from the core-supplying hole 45 is distributed into the respective core-forming nozzles 41a, and the sheath component supplied from the sheath-supplying hole 46 is supplied beyond the overflowing projections 46b into the sheath-forming nozzles to surround the cores. The sea component supplied from the sea-supplying opening 47 is supplied beyond the sea-overflowing projections 47b into the sea-forming nozzle holes, and thus a three-component concentric structure of core/sheath/sea is extruded from 43a in the form of a softened strand, and the extrudate is gathered and integrated at the gathering opening 49 having a circular or substantially circular section.

The multifilament type plastic optical fiber cable prepared according to the above-mentioned process has a novel structure heretofore not developed. Namely, the sections of the light transmitting paths acting have a substantially uniform circular shape, and the paths are arranged in a square-stacked structure or hexagonal staggered form structure in the light transmitting portion having a circular section. Accordingly, the light-transmitting characteristics of the respective light-transmitting paths are substantially uniform, and the image-transmitting characteristics of the multifilament type plastic optical fiber cable are greatly improved. Moreover, since the section of the image-transmitting portion of this multifilament type plastic optical fiber cable has a substantially circular section, there is no directivity of the flexural stress and the optical fiber is soft and flexible. Accordingly, even if an endoscope assembled by using this optical fiber cable as the image-transmitting member is inserted into the coronary arteries in the heart, the insertion can be accomplished very easily and since the optical fiber cable is not broken in any of the light-transmitting paths, a blood vessel endoscope having a very high safety factor can be provided.

When carrying out the present invention, it is not absolutely necessary for the light-transmitting paths constituting the multifilament type optical fiber cable used in the present invention to retain a core-sheath structure, and even a multifilament type optical fiber having a core-sheath two-component structure can be effectively cable used if the difference of the refractive index between the core-forming polymer and the sea-forming polymer is at least 0.01. Such a multifilament type plastic optical fiber cable can be prepared according to the above-mentioned process by using a spinneret having the same structure as shown in FIG. 4, except that the sheath-forming nozzle orifice is omitted.

To prevent a disturbance of the transmitted image by an intrusion of stray light into the optical fiber, a light-cutting covering layer is preferably formed on the periphery of the multifilament type optical fiber cable used as the image-transmitting member of the endoscope of the present invention. A black covering layer can be formed by coating a composition comprising a light-cutting pigment such as carbon black, lead oxide or a black organic pigment and polyethylene, polyvinyl chloride, polymethyl methacrylate, a vinylidene fluoride polymer, a tetrafluoroethylene polymer, a vinyl acetate/ethylene copolymer or a polyurethane on the periphery of the multifilament type optical fiber.

To precisely transmit the color of an object, preferably the coloration degree is low in the multifilament type optical fiber cable used as the image-transmitting member of the endoscope of the present invention. The coloration degree of the optical fiber can be determined by the YI value based on the wavelength dependency of the transmission loss of the optical fiber. The YI value can be calculated from the tristimulus values determined by JIS Z-8922-1971 according to the following formula:

$$YI = \frac{100(1.28X - 1.06Z)}{Y}$$

In the endoscope of the present invention, preferably the YI value of the image-transmitting member is smaller than 50, especially smaller than 30. In the case of an endoscope of the type where the observation is carried out through a television monitor, since color correction is possible, the allowable range of the YI value is expanded, and preferably the YI value is smaller than 80, especially smaller than 70.

Figure 6:
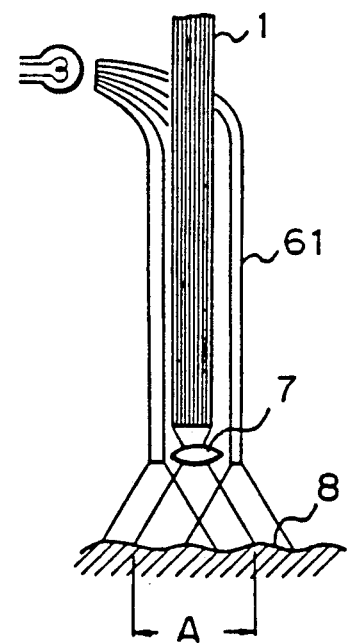

As the method of illuminating an object to be observed in the endoscope the present invention, there can be adopted a method in which at least one light guide having a high pliability and a diameter of 100 to 500 $\mu$ is arranged on the periphery of an image-transmitting multifilament type optical fiber cable 1, as shown in FIG. 1 or 6, or there can be adopted a method in which the same multifilamernt type optical fiber as used as the image-transmitting member is used as the light guide, as shown in FIG. 6. Moreover, there can be adopted a method in which a microlamp is arranged on the top end of an electric wire cable and an object to be observed is illuminated by this microlamp.

In the endoscope of the present invention, a multifilament type plastic optical fiber cable, in which light-transmitting paths having a circular or substantially circular section are arranged in a square-stacked structure or a hexagonal staggered form structure in the circular section of the light-transmitting portion so that the entire arrangement of the paths has a substantially circular shape, is used as the image-transmitting member, and therefore, the image-transmitting property is greatly improved and there is no directivity of bending. Due to this characteristic feature, the endoscope of the present invention is very advantageous in that the endoscope can be easily inserted in the narrow and curved coronary arteries of the heart. If both of the image-transmitting member and light guide are formed of plastics in the endoscope of the present invention, a disposal of the endoscope by burning becomes possible, and the breaking often occurring in case of a glass type optical fiber does not occur, and thus the endoscope has a very high safety factor. Therefore, the endoscope of the present invention is promising as a disposable blood vessel endoscope.

The present invention will now be described in detail with reference to the following examples.

EXAMPLES 1 THROUGH 3

By using a spinneret formed by assembling a core-forming orifice, a sheath-forming orifice and a sheath-forming orifice, as shown in FIG. 4, where 3043 nozzle holes were arranged in a hexagonal staggered form structure in a substantially circular region, multifilament type plastic optical fiber cable having characteristics shown in Table 1 were prepared by using polymethyl methacrylate having refractive index $n_1$ of 1.492 as the light-transmitting island-forming core component polymer, a polyfluoroalkyl methacrylate polymer having a refractive index $n_2$ of 1.415 as the sheath-forming component polymer and a vinylidene fluoride polymer having a refractive index of 1.402 as the sea-forming polymer. The properties of the obtained multifilament type optical fiber cable were measured, and the results are shown in Table 1. The numerical aperture (NA) was 0.472. By using the obtained three multifilament type optical fibers, endoscopes as shown in FIG. 1 were assembled by using 10 polymethyl methacrylate plastic optical fiber cable having a core diameter of 100 $\mu$ as the light guide and attaching an object lens to the top end of the image-transmitting member and an eyepiece to the rear end.

Bright images could be transmitted by the obtained endoscopes, and no anisotropy of bending was observed. Even after the repetition of the bending test, an increase of the number of dead fibers was not observed, and the initial image-transmitting characteristics could be maintained.

EXAMPLE 4

By using polymethyl methacrylate having a refractive index $n_1$ of 1.492 as the light-transmitting core-forming polymer and a vinylidene fluoride polymer having a refractive index of 1.402 as the sea-forming polymer, a multifilament type optical fiber having 3043 light transmitting paths were prepared in the same manner as described in Example 1 except that a spinneret constructed by removing the sheath-forming orifice from the structure shown in FIG. 4 was used. The properties of the obtained fiber were measured, and the results are shown in Table 1. The NA value was 0.51.

By using the obtained multifilament type optical fiber cable as the image-transmitting member, an endoscope was constructed in the same manner as described in Example 1, and the properties were measured. The results are shown in Table 1.

Even if the endoscope was repeatedly subjected to the bending test, none of the light-transmitting paths was broken and the handling property was very good.

EXAMPLE 5

A multifilament type optical fiber cable having characteristics shown in Table 1 was obtained in the same manner as described in Example 1 except that polymethyl methacrylate having a refractive index of 1.492 was used as the sea-forming polymer.

By using this optical fiber as the image-transmitting member, an endoscope was assembled in the same manner as described in Example 1. It was confirmed that a very sharp image was obtained.

TABLE 1

| Characteristics | | Example No. | | | | |
|---|---|---|---|---|---|---|
| | | 1 | 2 | 3 | 4 | 5 |
| Characteristics of multifilament type plastic optical fiber | Core diameter | 7 | 4 | 2.5 | 7 | 7 |
| | Outer diameter | 0.5 | 0.29 | 0.19 | 0.5 | 0.5 |
| | Core occupancy ratio (%) | 53 | 38 | 33 | 53 | 53 |
| | Transmission loss (dB/m) | 0.9 | 2.1 | 5.0 | 1.4 | 1.2 |
| | Used length | 2 | 2 | 1 | 2 | 2 |
| | Brightness index I | $3.2 \times 10^{-2}$ | $2.3 \times 10^{-2}$ | $7.2 \times 10^{-2}$ | $6.7 \times 10^{-2}$ | $6.7 \times 10^{-2}$ |
| Characteristics of endoscope | Image-transmitting property when endoscope was wound on rod having diameter of 10 mm | | | | | |
| | 3 turns | ○ | ○ | ○ | ○ | ○ |
| | 10 turns | ○ | ○ | ○ | ○ | ○ |
| | Resolving power (line pairs/mm) | 32.0 group 5, element 1 | 45.3 group 5, element 4 | 71.8 group 6, element 2 | 32.0 group 5, element 1 | 32.0 group 5, element 1 |

We claim:

1. An endoscope comprising as an image-transmitting member a multifilament type plastic optical fiber cable in which 50 to 20,000 light transmitting paths having a core diameter of 2 to 70 $\mu$m and a circular or substantially circular section are arranged in a hexagonal staggered form or square-stacked structure in a circular or substantially circular cable section, so that the configuration structure of the entire cores has a substantially circular shape in the section of the image-transmitting portion, wherein the same positional relationship of the ends of light-transmitting paths arranged in the section of the optical fiber cable is maintained on both the ends of the optical fiber cable, the periphery of the section of the image-transmitting portion of the optical fiber cable has a circular or substantially circular shape, and an object lens is attached to one end of the image-transmitting member and an image-transmitting light-receiving member is arranged on the other end of the image-transmitting member.

2. An endoscope as set forth in claim 1, wherein the light-transmitting portion of the multifilament type plastic optical fiber cable has a core-sheath structure, and the occupancy ratio of the area of the total cores to the sectional area of the light-transmitting portion in the section of the multifilament type plastic optical fiber cable is at least 30%.

3. An endoscope as set forth in claim 1 wherein the multifilament type plastic optical fiber cable has a resolution of at least 2 line pairs/mm as determined by using a test pattern of a resolution test target (USFA 1951).

4. An endoscope as set forth in claim 1, wherein the core diameter is 2 to 20 μm.

5. An endoscope as set forth in claim 1, wherein the number of light transmitting paths is 500 to 20,000.

6. An endoscope as set forth in claim 1, wherein the section of each light transmitting path has a hexagonal or more polygonal shape resembling a circular shape.

7. An endoscope as set forth in claim 1, wherein the light transmission loss of the multifilament type optical fiber cable is smaller than 6 dB/m.

8. An endoscope as set forth in claim 1, wherein the multifilament type optical fiber cable has a brightness index I of at least $2.0 \times 10^{-2}$.

9. An endoscope as set forth in claim 1, wherein a light-cutting covering layer is formed on the periphery of the multifilament type optical fiber cable.

10. An endoscope as set forth in claim 1, wherein at least one light guide is arranged on the periphery of the multifilament type optical fiber cable.

* * * * *